(12) United States Patent
Köhler

(10) Patent No.: US 6,183,500 B1
(45) Date of Patent: Feb. 6, 2001

(54) PROCESS AND APPARATUS FOR THE COSMETIC TREATMENT OF ACNE VULGARIS

(75) Inventor: Wolfgang Köhler, Schnaittach (DE)

(73) Assignee: SLI Lichtsysteme GmbH, Erlangen (DE)

( * ) Notice: Under 35 U.S.C. 154(b), the term of this patent shall be extended for 0 days.

(21) Appl. No.: 09/204,593

(22) Filed: Dec. 3, 1998

(51) Int. Cl.[7] .................................................. A61N 5/06
(52) U.S. Cl. .................................................. 607/88; 607/90
(58) Field of Search ............................... 607/88, 89, 91, 607/94, 90; 606/9, 12, 2

(56) References Cited

U.S. PATENT DOCUMENTS

| 4,930,504 | * | 6/1990 | Diamantopoulos et al. | 607/88 |
| 5,549,660 | * | 8/1996 | Mendes et al. | 607/88 |

* cited by examiner

*Primary Examiner*—Lee Cohen
*Assistant Examiner*—Nick Guy
(74) *Attorney, Agent, or Firm*—Brooks & Kushman P.C.

(57) ABSTRACT

A process and an apparatus for the cosmetic treatment of acne vulgaris utilize irradiation of the affected skin areas with light characterized by a combination of two emission spectra, one in a blue region and the other in a red region.

20 Claims, 4 Drawing Sheets

PROCESS AND APPARATUS FOR THE COSMETIC TREATMENT OF ACNE VULGARIS

TECHNICAL FIELD

This invention discloses a process for the cosmetic treatment of acne vulgaris by irradiation of the affected skin areas with light and an apparatus for the application of the process.

BACKGROUND ART

A known process uses UV light for the irradiation of the face. This, however, has the possible disadvantage of erythema formation or an undesirable oxidation of skin pigments.

Also known is a treatment with a cream containing approximately 0,5% benzoyl peroxide. The disadvantage of this treatment is possible skin dryness.

DISCLOSURE OF INVENTION

It is an object of the present invention to provide a process and an apparatus for the treatment of acne which not only eliminates the known disadvantages but also results in an excellent cosmetic effect.

BEST MODE FOR CARRYING OUT THE INVENTION

Figure 1:
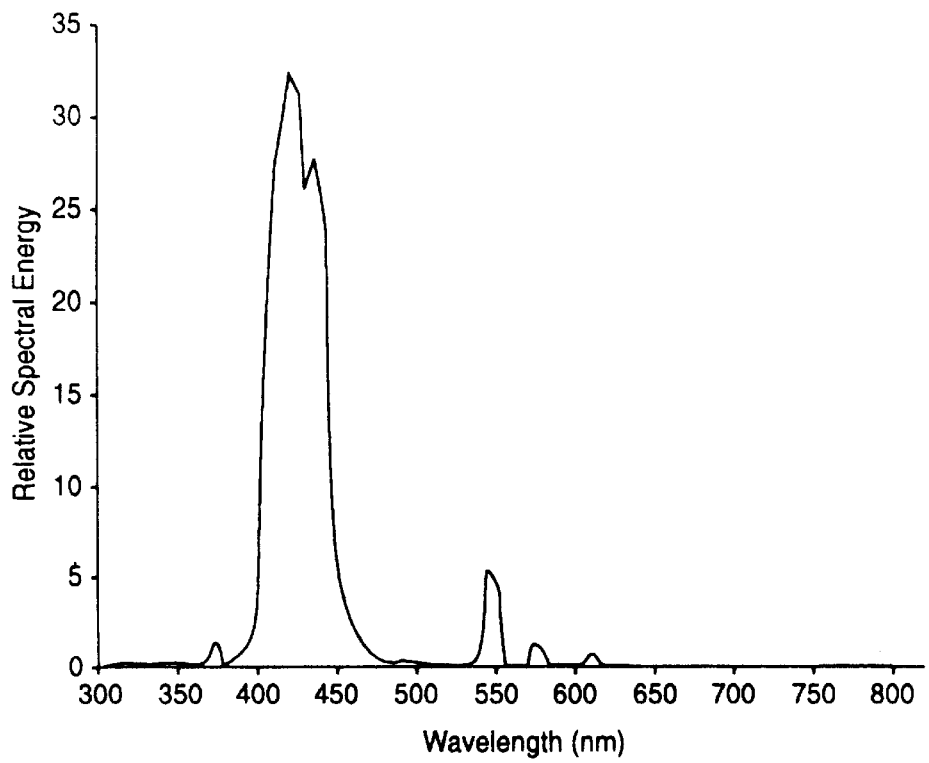
FIG. 1 shows the spectral energy distribution of a blue lamp according to the invention.
Figure 2:
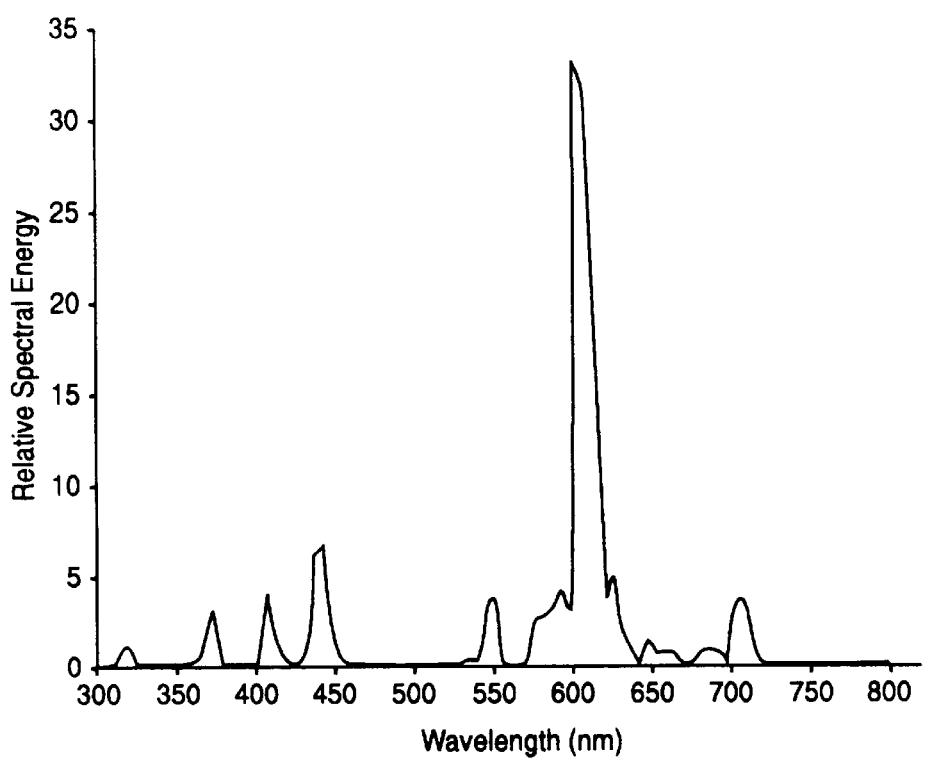
FIG. 2 shows the spectral energy distribution of a red lamp according to the invention.

This task is accomplished in accordance with the invention by applying light from low pressure mercury discharge (fluorescent) lamps having two different spectra, one in the blue range from 400 to 450 nm (FIG. 1), the other in the red range from 580 to 659 nm (FIG. 2).

Irradiation in accordance with the invention does not result in UV damage to the skin nor in significant skin dryness.

Figure 3:
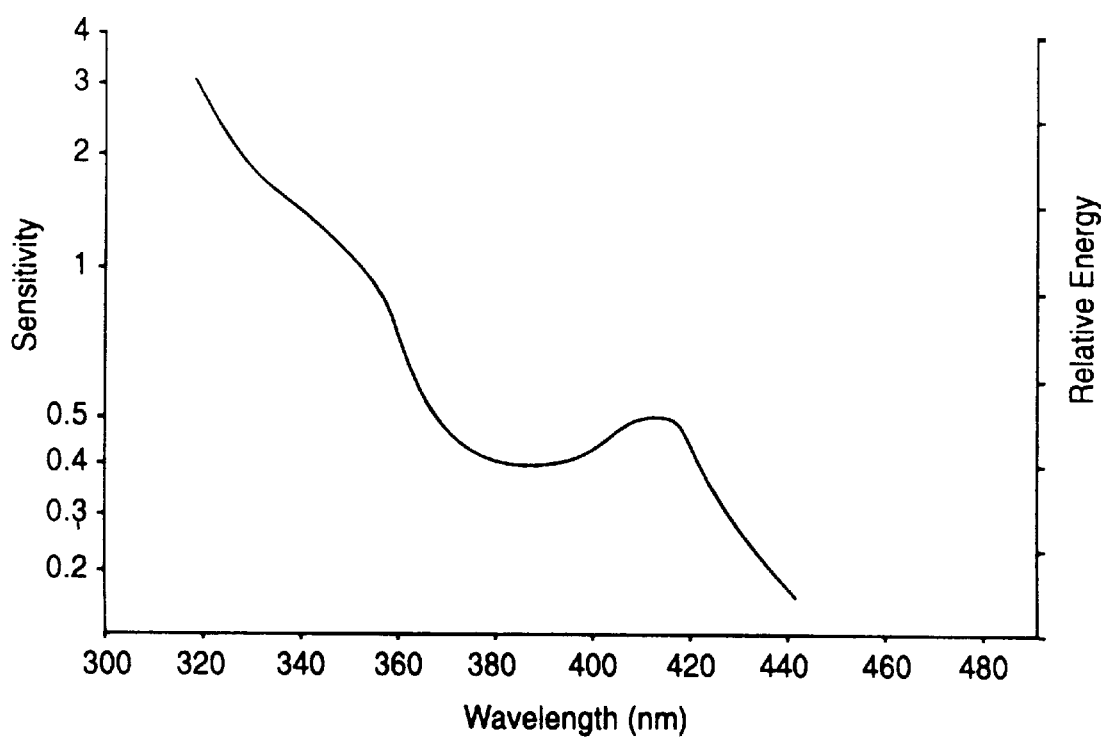
FIG. 3 shows the action spectrum for the inactivation of propionibacterium acne.

Both partial spectra in accordance with the invention are additive. The resulting spectrum is adapted to the action spectrum for the inactivation of the propionibacterium acne (FIG. 3). It has a biostimulating effect on the skin cells. This is caused by the fact that propionibacterium acne produces porphyrins which may be excited by short wavelength light. This has a lethal effect on the bacteria.

Light exposure studies were conducted with 61 patients having mild to moderate acne. They were treated with blue-red light in accordance with the invention and with blue light. The results were compared with white light exposure and treatment with benzoyl peroxide cream.

Patients were instructed to use the lamps for 15 minutes each day or apply the benzoyl peroxide cream twice daily.

Patient assessment was conducted every four weeks. The results are shown in the following table:

| Observation | Blue/Red Light | | Blue Light | | White Light | | Cream | |
|---|---|---|---|---|---|---|---|---|
| | Doctor % | Patient % | Doctor % | Patient % | Doctor % | Patient % | Doctor % | Patient % |
| worse/unchanged | 27 | 27 | 25 | 50 | 46 | 46 | 19 | 19 |
| slight/moderate improvement | 18 | 27 | 42 | 33 | 46 | 46 | 44 | 50 |
| significant improvement | 55 | 46 | 33 | 17 | 8 | 8 | 37 | 31 |

The number listed under "doctor" refers to a doctor's assessment, the number in the "patient" column is the patient's assessment after blue light or cream treatment.

Results show that the best results were obtained with mixed blue/red light in accordance with the invention with an average reduction of 66% in inflammatory and 42% in non-inflammatory lesions. With blue light the reduction was 50% and 32%, with white light 21% and 0% and with benzoyl peroxide cream 61% and 58%, respectively.

Investigators assessment showed a significant improvement, 55% with blue/red light, 33% with blue light, 21% with white light and 37% with cream treatment.

Patients assessment showed a significant improvement of 46% with blue/red light, 16% with blue light, 8% with white light and 31% after cream treatment. After light exposure dryness was negligible.

Figure 4:
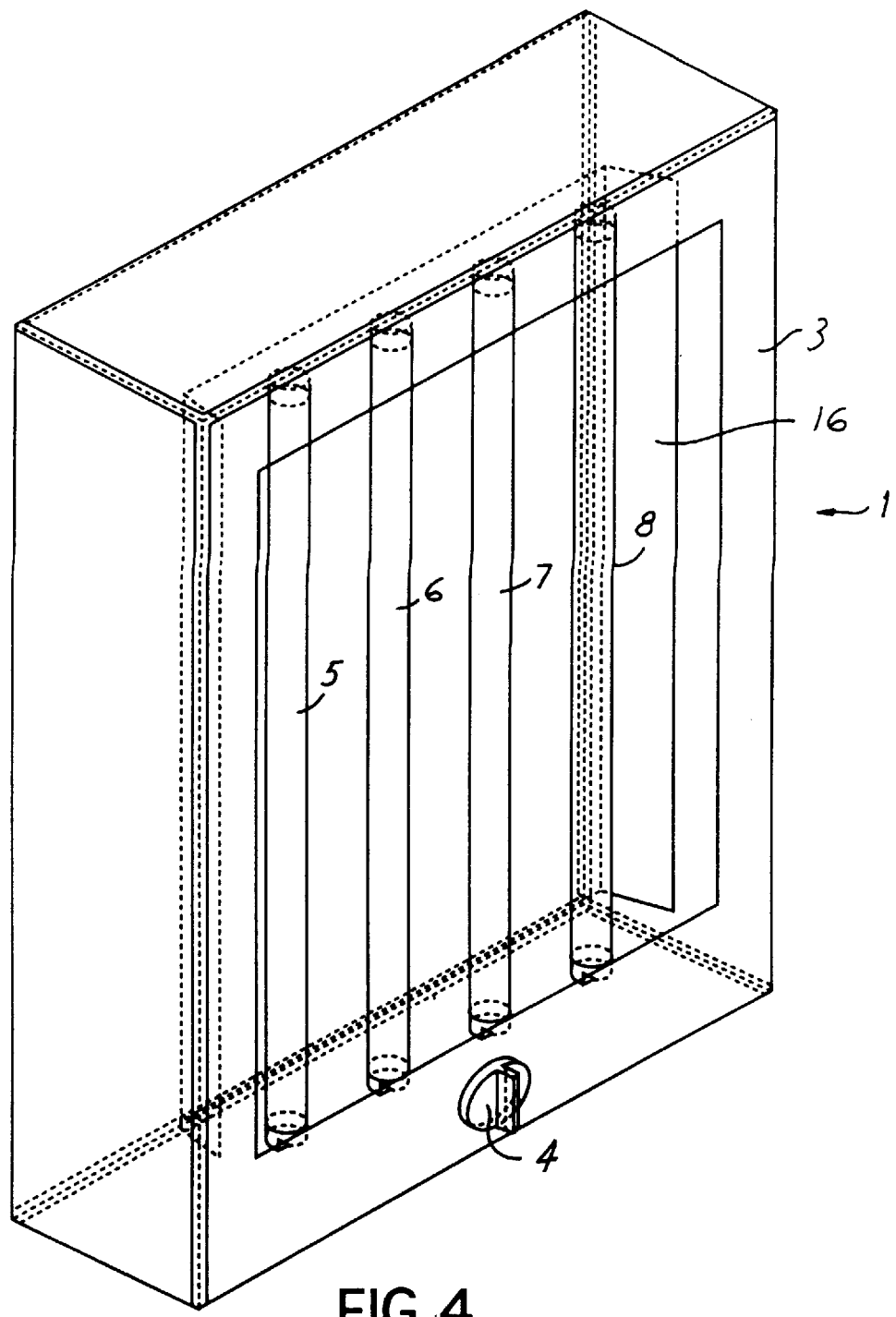
FIG. 4 shows an apparatus for the treatment of acne vulgaris in accordance with the invention including a housing 3, a timer switch 4, and double-ended fluorescent lamps 5, 6, 7, 8.

The apparatus 1 as shown in FIG. 4 is provided with at least one blue and red lamp, each having a spectrum in accordance with FIGS. 1 or 2, respectively. The lamps are of the double-ended low pressure mercury discharge (fluorescent) type, according to IEC Publication 60081. The embodiment in FIG. 4 shows four lamps 5, 6, 7, 8, arranged in parallel, having a bulb diameter of 15 to 40 mm and a length of 300 to 600 mm. Two of the lamps emit in the blue range, the other two in the red part of the spectrum. The arrangement of the lamps in the apparatus 1 is such that blue and red lamps alternate. In FIG. 4, lamps 5 and 7 have blue, lamps 6 and 8 red emission.

Figure 5:
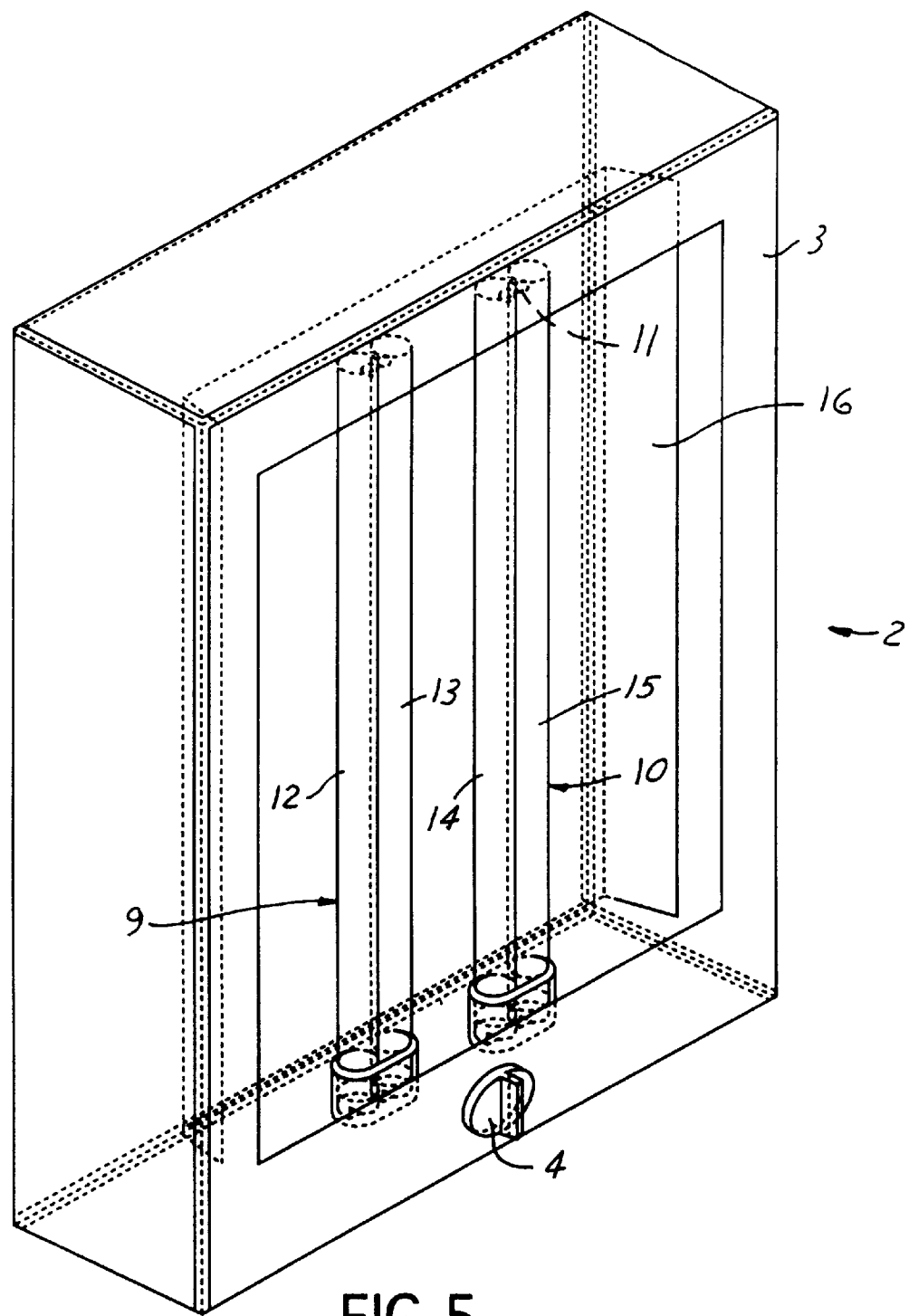
FIG. 5 shows an alternative embodiment of the apparatus shown in FIG. 4 which includes housing 3, timer switch 4, and single-ended fluorescent lamps 9, 10.

The embodiment of the apparatus 2 in FIG. 5 shows two single-ended fluorescent lamps 9, 10, according to IEC Publication 60901. Each lamp consists of two legs 12, 13 and 14, 15, which are joined together by means of a hollow glass tube 11 located opposite the base end, or by a U-bent tube sealed to both legs at the end opposite the base. The total length of each lamp is between 225 to 414 mm, one leg of each lamp is coated with blue, the other leg with red phosphor in accordance with the invention.

To increase the irradiation efficiency, an external reflector 16 is provided between each lamp and the housing 3 such that the light is preferentially emitted in the forward direction. Alternatively, two or more lamps are provided with a common reflector. Still another alternative is to apply the reflector as a reflective coating onto the inner bulb wall of a lamp between the glass and phosphor coating as internal reflector.

Penetration depth of red light into the skin increases as from 600 nm up, depending also on the type of skin. Further, red light of longer wave lengths has a healing effect. To accommodate for this, variation of the intensity ratio of red to blue light can be advisable. Such accommodation in accordance with the invention can be effected by use of combinations of one blue with three red or one red with three blue lamps alternatively.

Each lamp can be operated on a dimmable ballast which allows for adjustment of the light intensity from 10 to 100% of the nominal value.

Blue light and red light at shorter wavelengths may be detrimental to acnes bacteria within certain exposure times and red/blue intensity ratios.

What is claimed is:

1. A process for the cosmetic treatment of acne vulgaris, the process including:
    irradiating affected skin areas with light characterized by a combination of two emission spectra, one in a blue region from 400 to 450 nm and the other in a red region from 580 to 659 mn.

2. The process according to claim 1, wherein the red region is from 580 to 630 nm.

3. The process according to claims 1 or 2, wherein the irradiating step is conducted once per day for about 15 minutes.

4. An apparatus for the cosmetic treatment of acne vulgaris, the apparatus comprising:
    a housing; and
    two or more lamps disposed within the housing, the lamps for irradiating affected skin areas with light characterized by a combination of two emission spectra, one in a blue region from 400 to 450 nm and the other in a red region from 580 to 659 nm.

5. The apparatus according to claim 4, wherein the lamps are arranged substantially parallel to each other.

6. The apparatus according to claim 4, wherein the lamps include four double-ended fluorescent lamps.

7. The apparatus according to claim 6, wherein the lamps have a bulb diameter of 15 to 40 mm and a length of 300 to 600 mm.

8. The apparatus according to claim 6, wherein a first two of the four lamps emit light in the blue region and a second two of the four lamps emit light in the red region.

9. The apparatus according to claim 8, wherein the lamps are arranged such that the first two lamps emitting light in the blue region and the second two lamps emitting light in the red region alternate.

10. The apparatus according to claim 6, wherein the lamps include one lamp that emits light in the blue region and three other lamps that emit light in the red region.

11. The apparatus according to claim 6, wherein the lamps include one lamp that emits light in the red region and three other lamps that emit light in the blue region.

12. The apparatus according to claim 4, wherein the two or more lamps include two single-ended fluorescent lamps, each lamp having two legs which are joined together by a tube.

13. The apparatus according to claim 12, wherein the lamps have a length of 225 to 414 mm.

14. The apparatus according to claim 12, wherein one leg of each lamp emits light in the blue region and the other leg of each lamp emits light in the red region.

15. The apparatus according to claim 12, wherein one lamp has two legs that emit light in the blue region and the other lamp has one leg that emits light in the blue region and another leg that emits light in the red region.

16. The apparatus according to claim 12, wherein one lamp has two legs that emit light in the red region and the other lamp has one leg that emits light in the blue region and another leg that emits light in the red region.

17. The apparatus according to claim 4, further comprising at least one reflector arranged between each lamp and the housing for increasing the irradiation efficiency.

18. The apparatus according to claim 17, wherein the at least one reflector includes a reflective coating provided on an inner bulb wall of each lamp.

19. The apparatus according to claim 6, further comprising a timer switch in communication with the lamps for limiting the exposure time of affected skin areas to irradiation.

20. The apparatus according to claim 6, wherein the lamps are operated on a dimmable ballast to allow for adjustment of the light intensity.

* * * * *